(12) United States Patent
Mimura et al.

(10) Patent No.: US 11,360,007 B2
(45) Date of Patent: Jun. 14, 2022

(54) EMBEDDING APPARATUS

(71) Applicants: SAKURA SEIKI CO., LTD., Nagano (JP); SAKURA FINETEK JAPAN CO., LTD., Tokyo (JP)

(72) Inventors: Masahisa Mimura, Nagano (JP); Yoshiaki Nakazawa, Nagano (JP); Mitsuaki Narita, Nagano (JP)

(73) Assignees: SAKURA SEIKI CO., LTD., Nagano (JP); SAKURA FINETEK JAPAN CO., LTD., Tokyo (JP)

( * ) Notice: Subject to any disclaimer, the term of this patent is extended or adjusted under 35 U.S.C. 154(b) by 93 days.

(21) Appl. No.: 17/044,785

(22) PCT Filed: May 21, 2019

(86) PCT No.: PCT/JP2019/020019
§ 371 (c)(1),
(2) Date: Oct. 1, 2020

(87) PCT Pub. No.: WO2020/021830
PCT Pub. Date: Jan. 30, 2020

(65) Prior Publication Data
US 2021/0190651 A1 Jun. 24, 2021

(30) Foreign Application Priority Data
Jul. 25, 2018 (JP) .............................. JP2018-139203

(51) Int. Cl.
*G01N 1/00* (2006.01)
*G01N 1/36* (2006.01)
*G01N 33/48* (2006.01)

(52) U.S. Cl.
CPC ............... *G01N 1/36* (2013.01); *G01N 33/48* (2013.01)

(58) Field of Classification Search
None
See application file for complete search history.

(56) References Cited

U.S. PATENT DOCUMENTS

2011/0076753 A1 3/2011 Goerner et al.
2017/0036211 A1* 2/2017 Schneider .............. A61B 17/30

FOREIGN PATENT DOCUMENTS

JP 2002318177 A 10/2002

OTHER PUBLICATIONS

Japan Patent Office, International Search Report issued in parent International Patent Application No. PCT/JP2019/020019, dated Aug. 6, 2019, (including English translation of ISR), 6 pages.

(Continued)

*Primary Examiner* — Jyoti Nagpaul
(74) *Attorney, Agent, or Firm* — William Thomas Babbitt, Esq.; Leech Tishman Fuscaldo & Lampl

(57) ABSTRACT

The present invention addresses an object to provide an embedding apparatus capable of removing an embedding material such as paraffin and solids such as debris of a tissue fragment adhered to a tweezers holder hole easily. As a solving means, an embedding apparatus (10) includes: a tweezers holder (26) including a tweezers holder hole (26a); a first heater (34) configured to warm the tweezers holder (26); a first sensor (40) configured to detect a temperature of the tweezers holder (26); and a control unit (46) wherein the control unit (46) performs control to turn the first heater (34) OFF until the temperature reaches a point equal to or below a first set temperature at which the embedding material adhered to the tweezers holder hole (26a) starts to solidify, and upon receipt of a signal indicating that the temperature of the tweezers holder (26) reaches the first set temperature from the first sensor (40), turn the first heater (34) ON until the temperature reaches a second set temperature at which a (Continued)

sticking site between the solidified embedding material and the tweezers holder hole (26a) is melted.

4 Claims, 5 Drawing Sheets

(56) References Cited

OTHER PUBLICATIONS

URL:https://www.sakurajp.com/db/item/document/documents00070-1.pdf TEC5-EM-02 [Online], Nov. 2017, Manufacture/Sale Notice No. 20BX00014000002, 1-2, Name of Parts and User Maintenance/Inspection Matters, Pin Set Holder. Sakura Finetek Japan Co., Ltd. Tissue-Tek TEC Embedding Module.

* cited by examiner

EMBEDDING APPARATUS

CROSS-REFERENCE TO RELATED APPLICATIONS

The present Application is a national stage of International Patent Application No. PCT/JP2019/020019, titled "Embedding Device," filed May 21, 2019, which claims priority from Japanese Patent Application No. 2018-139203, filed Jul. 25, 2018, the contents of which are incorporated in this disclosure by reference in their entirety.

TECHNICAL FIELD

The present invention relates to an embedding apparatus and, more specifically, to an embedding apparatus configured to embed a sample such as a tissue fragment by using an embedding material such as paraffine.

BACKGROUND ART

To prepare a microscopic specimen from a tissue fragment (sample) collected from human body or the like, a collected tissue fragment is dehydrated by alcohol using a tissue fragment processing apparatus, then the alcohol is substituted into xylene, and the substituted tissue fragment is embedded with an embedding material such as paraffine infiltrated therein. The embedded tissue fragment is then sliced with a Microtome or the like to make a microscopic specimen.

Note that when slicing the tissue fragment embedded with the embedding material with Microtome, how to hold a soft tissue fragment becomes an issue. In addition, from the necessity of description of data indicating when, from whom, from which part of a body the tissue fragment was collected, an embedding apparatus configured to attach the tissue fragment embedded by the embedding material integrally with a body of a resin cassette by the embedding material is proposed (see PTL 1: JP-A-2002-318177)

CITATION LIST

Patent Literature

PTL 1: JP-A-2002-318177

SUMMARY OF INVENTION

Technical Problem

A schematic process for embedding a sample by using the embedding apparatus exemplified in PTL 1 is as follows. First, a cassette including a sample accommodated in a molten paraffine in one warming tank is taken and a size of the sample is confirmed. Next, an embedding tray which is suitable for the size of the sample from the other warming tank is taken and a small amount of paraffin is dispensed from a needle valve into the embedding tray. Next, the sample in the cassette is put into the embedding tray, and the position of the sample is fixed while cooling the embedding tray on a cold spot. Next, an opening of the embedding tray is covered with a body of the cassette with a lid removed, and the molten paraffin is dispensed from above the body of the cassette.

Schematically, the process of embedding the sample is performed as described above, and tools such as tweezers are used in particular for transferring and fixing the position of the sample. Such tools, when not used, are accommodated, with a distal end thereof being inserted into a tweezers holder hole in a warmed tweezers holder, so that the position of the sample can be fixed without causing the molten paraffine adhered to the distal end set (solidified) when used.

Therefore, the tweezers holder hole is subjected to repeated insertion and retraction of tools such as tweezers with the tissue fragment and the paraffin adhered thereto throughout the embedding process, and thus debris of the tissue fragment, the paraffin, and the like are gradually accumulated (adhered). Therefore, a user has been required to remove such debris by wiping them off with tissues as needed. In particular, since the tweezers holder hole is warmed, the adhered paraffin is melted and thus is accumulated in the tweezers holder hole in a liquid state, and solids such as debris of the tissue fragment are deposited at a bottom. Therefore, the user needs to suck liquid such as the molten paraffin at first, and then remove the solids at the bottom, which is duplication of work.

Solution to Problem

In view of such circumstances, it is an object of the present invention to provide an embedding apparatus capable of removing an embedding material such as paraffin and solids such as debris of a tissue fragment adhered to a tweezers holder hole easily.

The present invention solves the above problems by means of a solution as described below in one embodiment.

An embedding apparatus according to the present invention equipped with a hot plate configured to warm an embedding tray; and a dispenser configured to dispense an embedding material in the embedding tray warmed by the hot plate comprising: a tweezers holder having one or a plurality of tweezers holder holes in which distal ends of tweezers are accommodated; a first heater configured to warm the tweezers holder; a first sensor configured to detect a temperature of the tweezers holder; and a control unit configured to perform temperature control of the first heater, wherein the control unit performs control to turn the first heater OFF until the temperature reaches a point equal to or below a first set temperature at which the embedding material adhered to the tweezers holder hole starts to solidify, and upon receipt of a signal indicating that the temperature of the tweezers holder reaches the first set temperature from the first sensor, turn the first heater ON until the temperature reaches a second set temperature at which a sticking site between the solidified embedding material and the tweezers holder hole is melted.

In this configuration, by turning the heater OFF and letting the tweezers holder be cooled until the temperature reaches the first set temperature by the control unit in a state in which a tool such as tweezers are inserted into the tweezers holder hole, the embedding material such as paraffin adhered to the tweezers holder hole can be solidified around the tweezers or the like in a state in which solids such as debris of the tissue fragment is confined in an interior thereof. Subsequently, by turning the heater ON and warming the tweezers holder until the temperature reaches the second set temperature by the control unit, the sticking site between the solidified embedding material and the tweezers holder hole may be melted. By pulling the tweezers and the like out from the tweezers holder hole in this state, the solidified embedding material and the solids confined in the interior thereof can be removed in a state of being adhered to the tweezers and the like.

In addition, it is preferable that the control unit performs control to turn the first heater OFF upon receipt of a signal indicating that the temperature of the tweezers holder reaches the second set temperature from the first sensor, and turn the first heater ON upon receipt of a signal indicating that the temperature of the tweezers holder is lower than the second set temperature from the first sensor. This allows the sticking site between the solidified embedding material and the tweezers holder hole to be maintained in a melted state. Therefore, after the temperature of the tweezers holder has reached the second set temperature, the tweezers or the like can be pulled out at a given timing in a state in which the embedding material is solidified.

In addition, preferably, notification means configured to notify a user is provided and the control unit performs control to cause the notification means to perform notification upon receipt of the signal indicating that the temperature of the tweezers holder reaches the first set temperature from the first sensor, and in response to input information input by the user, turn the first heater ON until the temperature of the tweezers holder reaches the second set temperature. In this configuration, the user can recognize that the embedding material adhered to the tweezers holder hole is solidified, and thus can start melting of the sticking site between the solidified embedding material and the tweezers holder hole thereafter at a given timing.

In addition, preferably, the control unit performs control to cause the notification means to perform notification upon receipt of the signal indicating that the temperature of the tweezers holder reaches the second set temperature from the first sensor. This allows the user to recognize that the sticking site between the solidified embedding material and the tweezers holder hole is melted.

Advantageous Effects of Invention

According to the present invention, the embedding material such as paraffin can be solidified around the tool such as tweezers in a state in which the solid such as debris of the tissue fragment is confined in the interior thereof and then the sticking site between the embedding material and the tweezers holder hole can be melted. Therefore, by pulling the tool such as the tweezers out of the tweezers holder hole, the solidified embedding material and the solid confined therein can be easily removed in a state of being adhered to the tool.

DESCRIPTION OF EMBODIMENTS

Figure 1:
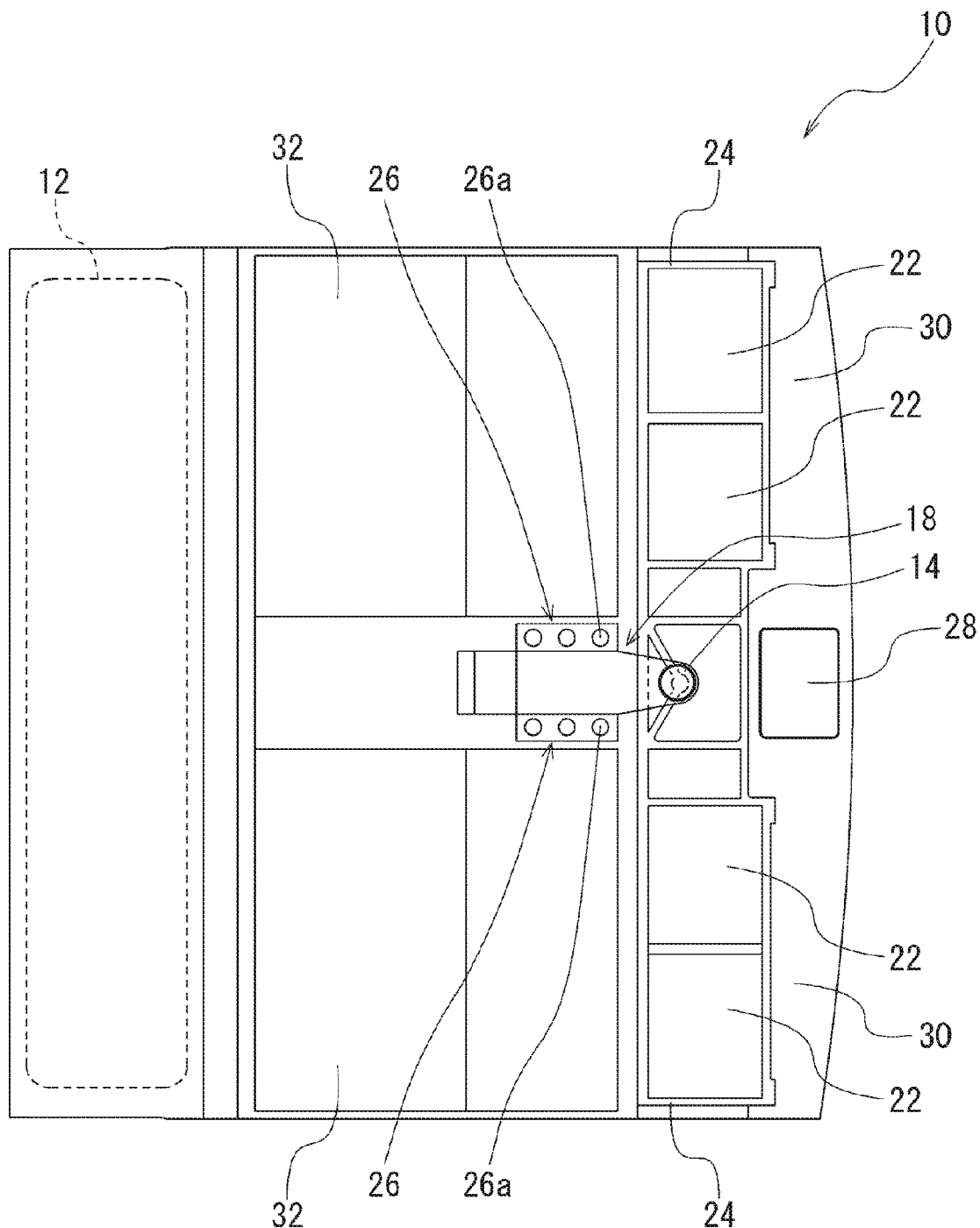
FIG. 1 is a schematic drawing (plan view) illustrating an example of an embedding apparatus according to an embodiment of the present invention.
Figure 2:
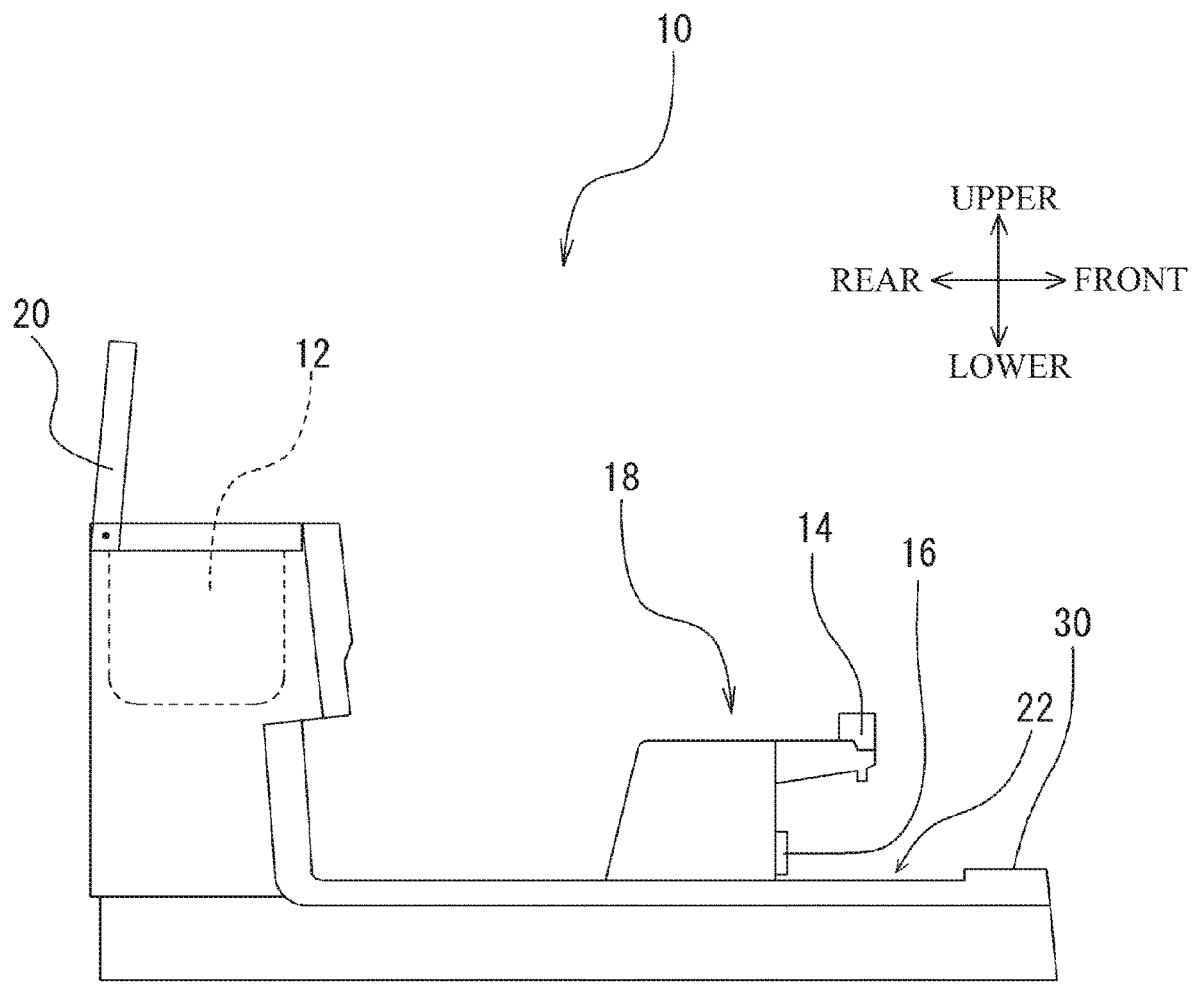
FIG. 2 is a schematic drawing (side view) illustrating an example of the embedding apparatus illustrated in FIG. 1.
Figure 3:
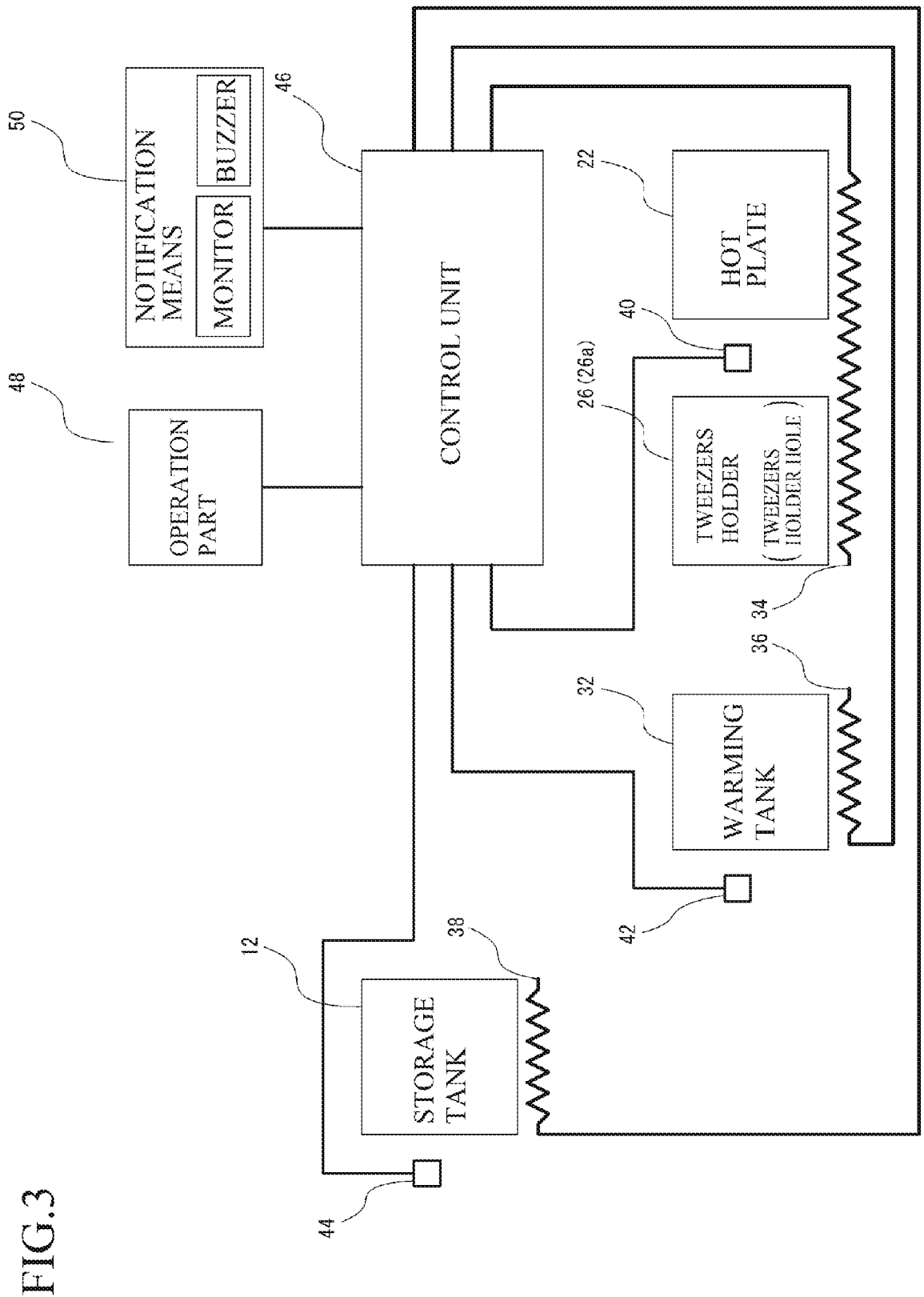
FIG. 3 is a schematic drawing (wiring system diagram) illustrating an example of the embedding apparatus illustrated in FIG. 1.

Referring to the drawings, an embodiment of the present invention will be described below in detail. FIG. 1 is a plan view (schematic drawing) illustrating an example of an embedding apparatus 10 according to the embodiment of the present invention, and FIG. 2 is a side view (schematic drawing) thereof. FIG. 3 is a wiring system diagram (schematic drawing) of the embedding apparatus 10. In all drawings, the same reference numerals will be given to members having the same function, and repeated description thereof will be omitted in some cases. Note that in the description of the present embodiments, paraffin is exemplified as an embedding material, and tweezers are exemplified as a tool used for transferring or fixing the position of a sample, respectively. However, the present invention is not limited thereto. In FIG. 1, the position where a user operate is defined as "front", the side opposite to the position where the user operates is defined as "rear", and left and light are defined as directions viewed from the user.

As illustrated in FIG. 1 and FIG. 2, the embedding apparatus 10 according to the present embodiment includes: a storage tank 12 in which paraffin as the embedding material is melted and stored, a needle valve 14 serving as a flow control valve located below the liquid level of the molten paraffin stored in the storage tank 12, and an open/close switch 16 for an open/close valve provided in a middle of piping connecting the storage tank 12 to the needle valve 14. Among these members, the needle valve 14 and the open/close switch 16 constitute a dispenser 18. Note that a cover 20 is mounted to be openable and closable over the storage tank 12, and a supply of paraffin or the like to the storage tank 12 can be performed by opening the cover 20.

In addition, a hot plate 22 configured to warm embedding trays or cassettes with a sample are provided on the left and right front of the dispenser 18. The hot plates 22 are partitioned by being surrounded at four sides thereof with a rail-type inflow groove 24. The inflow groove 24 allows leaked paraffin to flow therein and to be stored in a waste liquid paraffin tray (not illustrated) provided at a lower portion.

In contrast, tweezers holders 26 configured to warm the tweezers used for fixing the position of a tissue fragment are provided on the left and right of the dispenser 18. Each of the tweezers holders 26 includes three each of tweezers holder holes 26a along the fore-and-aft direction for inserting the tweezers.

Further, a cold spot 28 to be cooled by a Peltier element is provided in front of the dispenser 18. The cold spot 28 is used to solidify molten paraffin filled in an embedding tray in which a sample is accommodated. In addition, a hand rest portion 30 for allowing the user to rest hands is provided on the left and right of the cold spot 28.

In contrast, a warming tank 32 configured to accommodate and warm the embedding trays or the cassettes with a sample is provided on the left and right rear of the dispenser 18.

Figure 4:
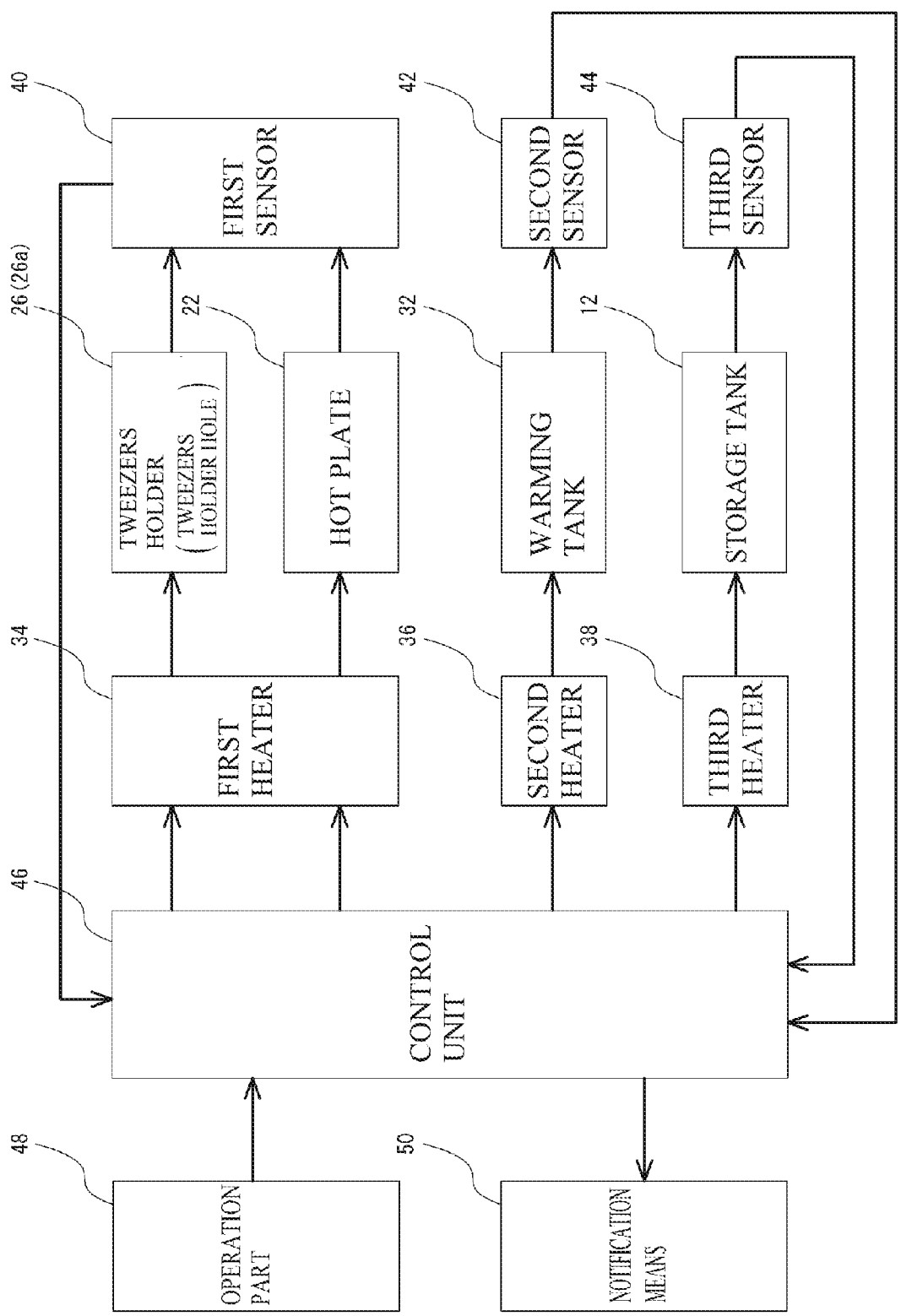
FIG. 4 is a block diagram illustrating an example of a control mechanism of the embedding apparatus illustrated in FIG. 1.

Note that in order to allow an operator to perform the operation regardless of the dominant hand (right hand, left hand) of the operator, the embedding apparatus 10 is configured such that each mechanism is arranged symmetrically with respect to the dispenser 18. In addition, an operation part 48 for maneuvering and setting of an operation is provided on a display device connected to a main body of the embedding apparatus 10 or the embedding apparatus 10 (FIG. 3 and FIG. 4).

Subsequently, a heater configured to warm the embedding apparatus 10 and a sensor configured to detect the temperature will be described. As illustrated in FIG. 3, a first heater 34 is laid for the tweezers holder 26, the hot plate 22 continued therefrom, and a portion in the vicinity thereof, and cables thereof are connected to a control unit 46. The control unit 46 includes a CPU and a memory and operates based on an operation program set in advance and set signals input from the operation part 48. Therefore, according to the configuration described above, the operation (ON and OFF) of the first heater 34 can be controlled by the control unit 46 and, by means of this, the temperature control of the tweezers holders 26 including the tweezers holder holes 26*a* and the hot plate 22 is achieved. In addition, a first sensor 40 serving as a temperature sensor is mounted on the tweezers holder 26 and the hot plate 22, and the cables thereof are connected to the control unit 46. Accordingly, the temperature change of the tweezers holders 26 and the hot plate 22 due to the operation control of the above-described first heater 34 can be fed back to the control unit 46. Note that the position and the number of the first sensor 40 and the first heater 34 are not limited and, for example, these members may be mounted only on the hot plate 22 and configured to control the temperature of the tweezers holders 26 indirectly.

In addition, a heater different from the first heater 34 is laid for a configuration (portion) other than the tweezers holders 26, the hot plate 22 continuing thereto of the embedding apparatus 10, and the portion in the vicinity thereof, and a sensor different from the first sensor 40 is mounted. For example, the warming tank 32 illustrated in FIG. 3 is provided with a second heater 36 and a second sensor 42, and the storage tank 12 is provided with a third heater 38 and a third sensor 44, respectively. Cables of these heaters and sensors are connected respectively to the control unit 46. Accordingly, the temperature control for the tweezers holders 26 and the hot plate 22 having the first heater 34 laid therefor may be performed separately from that for the warming tank 32, the storage tank 12, and other configurations. In addition, since such separate temperature controls can be performed at the same time, heating or cooling the tweezers holders 26 and the hot plate 22 is enabled in a state in which the warming tank 32, the storage tank 12, and other configurations are maintained constantly at a predetermined temperature as described later. Note that the positions and the numbers of the heaters and the sensors in the configuration (portion) other than the tweezers holders 26, the hot plate 22 continuing thereto as well as the portion in the vicinity thereof are illustrative only, and are not limited as long as at least the heater separate from the first heater 34 is laid and a sensor different from the first sensor 40 is mounted. In addition, reference numeral 50 denotes notification means, and is connected to the control unit 46 together with the operation part 48 via their respective cables.

Figure 5:
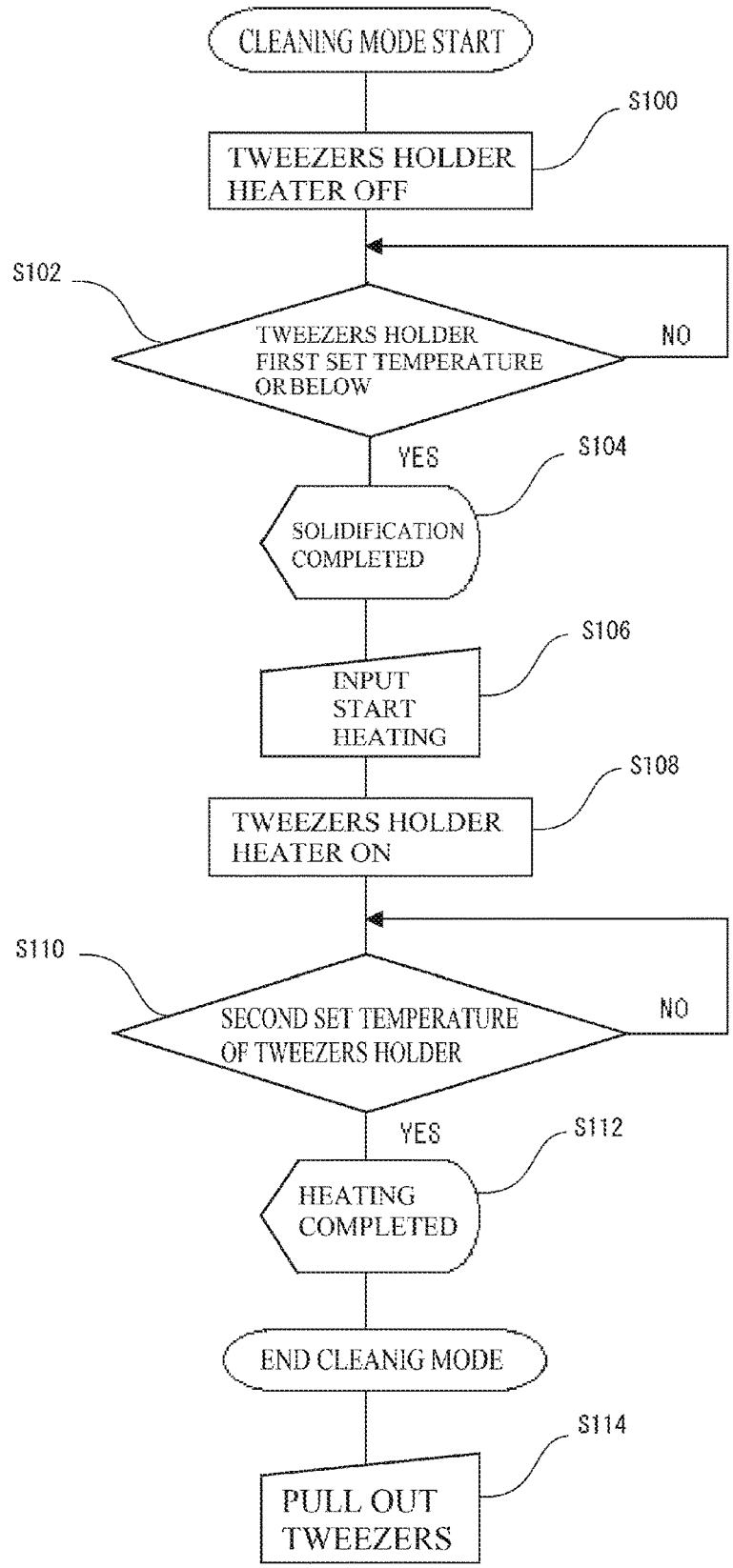
FIG. 5 is a flowchart illustrating an example of a control operation of the embedding apparatus illustrated in FIG. 1.

Subsequently, control to be performed by the control unit 46 will be described. FIG. 4 is a block diagram illustrating an example of a control mechanism of the embedding apparatus 10. FIG. 5 is a flowchart illustrating an example of the control operation of the embedding apparatus 10.

In a case where the embedding material such as paraffin and solids such as debris of the tissue fragment are accumulated in the tweezers holder hole 26*a* of the embedding apparatus 10 as a result of embedding, the user selects "cleaning mode" on the operation part 48. Accordingly control by the control unit 46 that receives the input information is started as described below.

First, the control unit 46 performs control to turn the first heater 34 OFF (S100). Accordingly, the tweezers holders 26 including the tweezers holder holes 26*a* having the first heater 34 laid therefor and warmed so far start to be cooled. The control unit 46 constantly receives a signal from the first sensor 40 and constantly receives an input of information on the temperature of the tweezers holders 26. Consequently, when a signal indicating that the temperature of the tweezers holders 26 reaches (lowers) a first set temperature (or below) is received (S102), the control unit 46 performs control to notify the notification means 50 that the solidification is completed (S104).

As used herein the term "the first set temperature" is intended to mean a preset temperature at which paraffin adhered to the tweezers holder holes 26*a* solidifies (sets), which can be set and changed via the operation part 48. While embedding is performed, since the tweezers holder holes 26*a* are warmed, the paraffin adhered to the tweezers holder holes 26*a* are melted and thus are accumulated in the tweezers holder holes 26*a* in a liquid state, and solids such as debris of the tissue fragment are deposited at the bottom. Accordingly, by cooling the tweezers holder holes 26*a* to the first set temperature with the tweezers inserted in the tweezers holder hole 26*a*, the molten paraffin accumulated in the tweezers holder hole 26*a* can be solidified around the tweezers in a state in which the solids are confined therein.

Note that although the notification from the notification means 50 allows the user to recognize that solidification of the molten paraffin has completed, a configuration in which such notification is not performed is also applicable. Specifically, notification in the embodiment illustrated in FIG. 3 is achieved by displaying ("solidification completed" display) on a monitor, and activating a buzzer, but is not limited thereto. The entire or part of the notification means 50 may be integrated with the operation part 48.

Next, by an input to the operation part 48 by the user (S106), the control unit 46 that has received the input information performs control to turn the first heater 34 ON (S108). Accordingly, the tweezers holders 26 including the tweezers holder holes 26*a* cooled so far start to be warmed (heated). This control, being configured to be started upon receipt of the input information from the user, can be started at a given timing. However, for example, a configuration in which control to turn the first heater 34 ON is started upon receipt of the signal indicating that the temperature of the tweezers holders 26 reaches the first set temperature from the first sensor 40 is also applicable.

Upon receipt of a signal indicating that the temperature of the tweezers holders 26 reaches a second set temperature from the first sensor 40 after the first heater 34 has turned ON and warming of the tweezers holders 26 is started (S110), the control unit 46 performs control to notify the notification means 50 that the heating is completed (S112). Accordingly, the "cleaning mode" by the control unit 46 is terminated. From then onward, control to turns the first heater 34 selectively ON and OFF is performed according to the signal from the first sensor 40 so that the temperature of the tweezers holders 26 is maintained at the second set temperature. In other words, control is performed to turn the first heater 34 OFF upon receipt of a signal indicating that the temperature of the tweezers holders 26 reaches the second set temperature from the first sensor 40, and turn the first heater 34 ON upon receipt of the signal indicating that the temperature of the tweezers holders 26 is lower than the second set temperature from the first sensor 40.

As used herein the term "the second set temperature" is intended to mean a preset temperature at which sticking site between the solidified paraffin and the tweezers holder hole 26*a* melts, which can be set and changed via the operation part 48. The molten paraffin is solidified around the tweezers by cooling the tweezers holders 26 to the first set temperature. However, in this state, since the solidified paraffin is secured to the tweezers holder hole 26*a*, the tweezers cannot be pulled out. Therefore, by warming the tweezers holder holes 26a, the solidified paraffin starts to be melted from the periphery which is a portion that is in direct contact with the tweezers holder hole 26a. Subsequently, when the tweezers holder holes 26a reach the second set temperature, the sticking site between the solidified paraffin and the tweezers holder hole 26a is melted, so that the tweezers can be pulled out from the tweezers holder hole 26a (S114). At this time, since the paraffin solidified by cooling is adhered to the periphery of the tweezers, the embedding material and the solid confined therein can be removed easily from the tweezers holder hole 26a by pulling out the tweezers. Accordingly, cleaning of the tweezers holder hole 26a is terminated.

Note that although the notification from the notification means 50 allows the user to recognize that the sticking site between the solidified paraffin and the tweezers holder hole 26a is melted, a configuration in which such notification is not performed is also applicable. Specifically, notification in the embodiment illustrated in FIG. 3 is achieved by displaying ("heating completed" display) on a monitor, and activating a buzzer, but is not limited thereto. The entire or part of the notification means 50 may be integrated with the operation part 48.

In addition, since the temperature of the tweezers holder holes 26a are maintained at the second set temperature after the tweezers holder holes 26a have reached the second set temperature, the user does not have to pull out the tweezers immediately after the notification by the notification means 50, but can pull out at any timing.

The temperature control of the first heater 34 by the control unit 46 as described thus far ("cleaning mode") is performed for the tweezers holders 26 and the hot plate 22 continued therefrom as well as a portion in the vicinity thereof having the first heater 34 laid therefor. In contrast, for the warming tank 32, the storage tank 12, and other configuration having a heater different from the first heater 34 (the second heater 36, the third heater 38, and the like) laid therefor, control different from the control of the first heater 34 is performed via respective heaters. While the "cleaning mode" is performed, the control unit 46 performs control to always maintain the warming tank 32, the storage tank 12 and other configurations at a predetermined temperature at which the paraffin is melted via the different heaters (the second heater 36, the third heater 38, and the like). Consequently, even in a case where the embedding is stopped and the "cleaning mode" is performed, the embedding can be started again quickly by warming again only the tweezers holders 26 and the hot plate 22 continuing therefrom as well as the portion in the vicinity thereof associated with the first heater 34 relating to the corresponding control to the predetermined temperature at which paraffin melts after the cleaning of the tweezers holder holes 26a.

As described thus far, according to the embedding apparatus of the present invention, in a case where the embedding material such as paraffin and solids such as debris of the tissue fragments are accumulated in the tweezers holder hole, these debris can be removed easily by cooling or warming the tweezers holders via the temperature control of the heater by the control unit. In other words, by cooling the tweezers holders in a state in which a tool such as tweezers is inserted into the tweezers holder hole, the embedding material can be solidified around the tweezers or the like in a state in which solids such as debris of the tissue fragment confined therein. Subsequently, by warming the tweezers holders again and pulling out the tweezers or the like from the tweezers holder hole at a timing when the sticking site between the embedding material and the tweezers holder hole is melted, the solidified embedding material and the solids confined therein can be removed in a state of being adhered to the tweezers and the like.

In addition, according to the control unit, when the temperature reaches the temperature at which the sticking site between the solidified embedding material and the tweezers holder hole is melted (the second set temperature), the notification means is caused to provide notification and the temperature of the tweezers holder can be maintained at the second set temperature. Accordingly, the user can recognize that the sticking site between the solidified embedding material and the tweezers holder hole has melted and can pull out the tweezers or the like in a state in which the embedding material is solidified at a given timing.

In addition, according to the temperature control as described above, the first heater is laid for the tweezers holder and the hot plate continuing therefrom as well the portion in the vicinity thereof to control the temperature all at once, and a different heater is laid for other configuration, so that the paraffin is always maintained in a melted state. Accordingly, when the cleaning of the tweezers holder hole is terminated, the embedding can be started again quickly by warming again only the tweezers holders and the hot plate continuing therefrom as well as the portion in the vicinity thereof associated with the first heater to a predetermined temperature at which paraffin melts.

Note that the present invention is not limited to the embodiments described above and may be modified variously without departing the scope of the present invention.

What is claimed is:

1. An embedding apparatus equipped with a hot plate configured to warm an embedding tray and a dispenser configured to dispense an embedding material in the embedding tray warmed by the hot plate, the embedding apparatus comprising:
   a tweezers holder having one or a plurality of tweezers holder holes in which distal ends of tweezers are accommodated;
   a first heater configured to warm the tweezers holder;
   a first sensor configured to detect a temperature of the tweezers holder; and
   a control unit configured to perform temperature control of the first heater,
   wherein the control unit performs control to turn the first heater OFF until the temperature reaches a point equal to or below a first set temperature at which the embedding material adhered to the tweezers holder hole starts to solidify, and upon receipt of a signal indicating that the temperature of the tweezers holder reaches the first set temperature from the first sensor, turns the first heater ON until the temperature reaches a second set temperature at which a sticking site between the solidified embedding material and the tweezers holder hole is melted.

2. The embedding apparatus according to claim 1, wherein the control unit turns the first heater OFF upon receipt of a signal indicating that the temperature of the tweezers holder reaches the second set temperature from the first sensor, and turns the first heater ON upon receipt of a signal indicating that the temperature of the tweezers holder is lower than the second set temperature from the first sensor.

3. The embedding apparatus according to claim 1, comprising notification means configured to notify a user,
   wherein the control unit performs control to cause the notification means to perform notification upon receipt of the signal indicating that the temperature of the tweezers holder reaches the first set temperature from the first sensor, and turn the first heater ON upon receipt of input information input by the user until the temperature of the tweezers holder reaches the second set temperature.

4. The embedding apparatus according to claim 3, wherein the control unit performs control to cause the notification means to perform notification upon receipt of the signal indicating that the temperature of the tweezers holder reaches the second set temperature from the first sensor.

* * * * *